(12) United States Patent
Liu et al.

(10) Patent No.: US 10,467,495 B2
(45) Date of Patent: Nov. 5, 2019

(54) METHOD AND SYSTEM FOR LANDMARK DETECTION IN MEDICAL IMAGES USING DEEP NEURAL NETWORKS

(71) Applicant: Siemens Healthcare GmbH, Erlangen (DE)

(72) Inventors: David Liu, Plano, TX (US); Bogdan Georgescu, Plainsboro, NJ (US); Yefeng Zheng, Princeton Junction, NJ (US); Hien Nguyen, Pittsburgh, PA (US); Shaohua Kevin Zhou, Plainsboro, NJ (US); Vivek Kumar Singh, Princeton, NJ (US); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 63 days.

(21) Appl. No.: 15/564,036

(22) PCT Filed: May 11, 2015

(86) PCT No.: PCT/US2015/030084
§ 371 (c)(1),
(2) Date: Oct. 3, 2017

(87) PCT Pub. No.: WO2016/182551
PCT Pub. Date: Nov. 17, 2016

(65) Prior Publication Data
US 2018/0089530 A1     Mar. 29, 2018

(51) Int. Cl.
*G06K 9/46* (2006.01)
*G06K 9/62* (2006.01)
(Continued)

(52) U.S. Cl.
CPC ......... *G06K 9/4628* (2013.01); *G06K 9/627* (2013.01); *G06T 7/0012* (2013.01); *A61B 8/52* (2013.01); *G06K 2209/05* (2013.01)

(58) Field of Classification Search
CPC .. G06K 9/4628; G06K 9/627; G06K 2209/05; G06T 7/0012; A61B 8/52
See application file for complete search history.

(56) References Cited

U.S. PATENT DOCUMENTS 6,661,870 B2 * 12/2003 Kapatoes ............. A61N 5/1042
378/65
2009/0074272 A1 * 3/2009 Lu ......................... G06T 7/0012
382/128

(Continued)

OTHER PUBLICATIONS

Roth Holger et al ("A new 2.5D representation for lymph node detection using random sets of deep convention neural network observations", Sep. 14, 2014, Third international conference, Wuhan , China) (Year: 2014).*

(Continued)

*Primary Examiner* — Amara Abdi

(57) ABSTRACT

A method and system for anatomical landmark detection in medical images using deep neural networks is disclosed. For each of a plurality of image patches centered at a respective one of a plurality of voxels in the medical image, a subset of voxels within the image patch is input to a trained deep neural network based on a predetermined sampling pattern. A location of a target landmark in the medical image is detected using the trained deep neural network based on the subset of voxels input to the trained deep neural network from each of the plurality of image patches.

19 Claims, 4 Drawing Sheets

(51) Int. Cl.
   *G06T 7/00*     (2017.01)
   *A61B 8/08*     (2006.01)

(56) References Cited

U.S. PATENT DOCUMENTS

| | | | |
|---|---|---|---|
| 2014/0247977 A1* | 9/2014 | Han | G06K 9/34 |
| | | | 382/159 |
| 2015/0112182 A1* | 4/2015 | Sharma | A61B 5/0261 |
| | | | 600/408 |
| 2015/0269439 A1* | 9/2015 | Versace | G06K 9/00664 |
| | | | 382/103 |
| 2016/0019706 A1* | 1/2016 | Otomaru | G06T 7/73 |
| | | | 345/634 |

OTHER PUBLICATIONS

Krig, Scott: "Interest Point Detector and Feature Descriptor Survey", Computer Vision Metrics, May 26, 2014.

Mikolajczyk, et al.: "A performance evaluation of local descriptors", IEEE Transactions on Pattern Analysis and Machine Intelligence, IEEE Computer Society, USA, vol. 27, No. 10, Oct. 1, 2005, pp. 1615-1630.

Quoc V. Le, et al.: "Tiled convolutional neural networks", Advances in Neural Information Processing Systems 23, Dec. 31, 2010, pp. 1279-1287.

Roth, Holger R., et al.: "A New 2.5D Representation for Lymph Node Detection Using Random Sets of Deep Convolutional Neural Network Observations", Sep. 14, 2014, Grid and Cooperative Computing—GCC 2004: Third International Conference, Wuhan, China, Oct. 21-24, 2004 In: Lecture Notes in Computer Science, vol. 3251.

International Search Report for Corresponding Application PCT/US2015/030084, dated Feb. 8, 2016.

\* cited by examiner

METHOD AND SYSTEM FOR LANDMARK DETECTION IN MEDICAL IMAGES USING DEEP NEURAL NETWORKS

BACKGROUND OF THE INVENTION

The present invention relates to anatomical landmark detection in medical images, and more particularly, to anatomical landmark detection in medical images using deep neural networks.

Deep learning mimics the behavior of mammal brains in order to extract a meaningful representation from a high dimensional input. Data is passed through multiple layers of a network. The primary layers extract low-level cues, such as edges and corners for natural images. Deeper layers compose simple cues from previous layers into higher-level features. In this way, powerful representations emerge at the end of the network. The gradual construction of a deep network prevents the learning from be exposed to a high complexity of data too early. Several theoretical works show that certain classes of functions (e.g., indicator function) could be represented by a deep network, but require exponential computation for a network with insufficient depth.

Recently, deep learning has been applied with high accuracy to pattern recognition problems in images. Deep neural networks can be used in image related tasks, such as detection and segmentation. However, due to high computational costs during the evaluation phase, the computation time for deep neural network networks can be prohibitively large can prevents deep neural networks from being applied to many useful applications.

BRIEF SUMMARY OF THE INVENTION

The present invention provides a method and system for landmark detection in medical images. Embodiments of the present invention provide a method for applying deep neural networks for 3D landmark detection in 3D medical images in an efficient manner.

In an embodiment of the present invention, for each of a plurality of image patches centered at a respective one of a plurality of voxels in the medical image, a subset of voxels within the image patch is input to a trained deep neural network based on a predetermined sampling pattern. A location of a target landmark in the medical image is detected using the trained deep neural network based on the subset of voxels input to the trained deep neural network from each of the plurality of image patches.

These and other advantages of the invention will be apparent to those of ordinary skill in the art by reference to the following detailed description and the accompanying drawings.

DETAILED DESCRIPTION

The present invention relates to a method and system for landmark detection in medical images using deep neural networks. Embodiments of the present invention are described herein to give a visual understanding of the methods for landmark detection in medical images. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments of the present invention utilize deep neural networks trained directly on medical image data to learn complex image patterns and detect anatomical landmarks in the medical image data based on the complex image patterns. Deep neural networks are machine learning based neural networks with multiple hidden layers of learned features or variables between the input data and the output data. Deep neural networks will typically be implemented with three or more hidden layers. Deep neural networks are typically used in direct multi-class classification scenarios and are not typically applied to anatomical landmark detection tasks because the extension of deep neural networks to such anatomical landmark detection tasks can be quite computationally complex.

In a landmark detection task, a sliding window approach can be used, in which a large number of image patches are examined by sliding a window of a certain size over the whole image or volume. Deep neural networks operate directly on the image data in each image patch and each voxel or pixel in an image patch is typically input to a corresponding node of an input layer of the deep neural network. For practical reasons, an image patch size of 20×20×20 voxels can be used in isotropic 1 mm volumes, which results in an 8000 dimension input vector to the deep neural network. It is to be understood that the methods described herein are not limited to this particular image patch size, and may be similarly applied for any size image patch. For example, a 50×50×50 voxels image patch size can be used as well. The large size of the input vector to a deep neural network from such image patches makes straightforward use of such deep neural networks difficult for practical applications, such as landmark detection. Embodiments of the present invention provide methods for lowering a dimensionality of the input vector for a given image patch and thereby achieving speedup of landmark detection tasks using deep neural networks.

Figure 1:
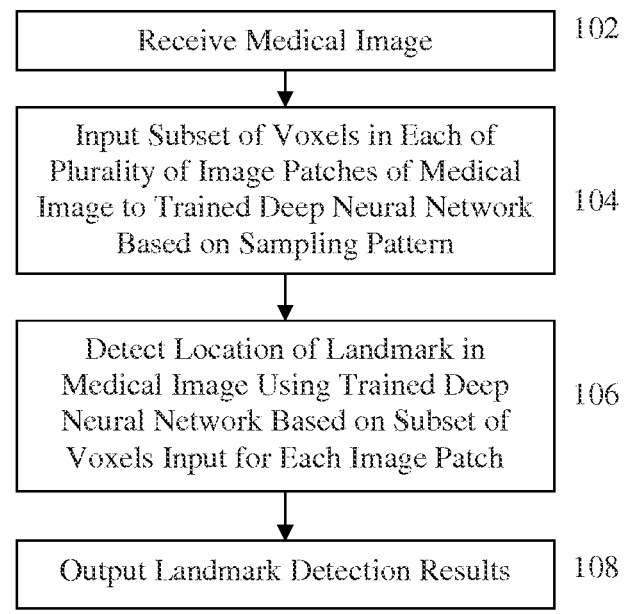
FIG. 1 illustrates a method for landmark detection in a medical image using a deep neural network according to an embodiment of the present invention.

FIG. 1 illustrates a method for landmark detection in a medical image using a deep neural network according to an embodiment of the present invention. The method of FIG. 1 transforms a medical image representing a patient's anatomy to detect landmarks, such as anatomical landmarks, in the medical image. At step 102, a medical image of a patient is received. In an advantageous embodiment, the medical image is a 3D medical image, which can also be referred to as a volume, but the present invention is not limited thereto and can be similarly applied to 2D medical images or 4D (3D+time) medical images as well. The description of the embodiments of the present invention generally treats the medical image as a 3D medical image refers to the elements of the medical image as voxels. It is to be understood the embodiments described herein can be similarly applied to 2D images and the term "pixel" can be substituted for "voxel" throughout the this disclosure. The medical image can be acquired using any type of imaging modality, such as computed tomography (CT), magnetic resonance imaging (MRI), ultrasound, x-ray fluoroscopy, position emission tomography (PET), Dyna CT, etc. The medical image may be received directly from an image acquisition device, such as a CT scanner, MR scanner, Ultrasound probe, PET scanner, etc., or may be received by loading medical image that was previously stored on a memory or storage of a computer system or by receiving the medical image via a network transmission from another computer system.

At step 104, a subset of voxels in each of a plurality of image patches of the medical image are input to a trained deep neural network classifier based on a sampling pattern. In an advantageous embodiment, a sliding window approach can be used to evaluate the plurality of image patches by sliding a window having a certain size over the whole 3D medical image. For example, the window can be centered at each voxel in the medical image, such that the resulting plurality of image patches includes a respective image patch centered at each voxel of the medical image. In an exemplary implementation, the size of each image patch can be 20×20×20 voxels for isotropic 1 mm medical image volumes, but the present invention is not limited thereto, and other size image patches (e.g., 50×50×50 voxels) can be used as well.

Figure 2:
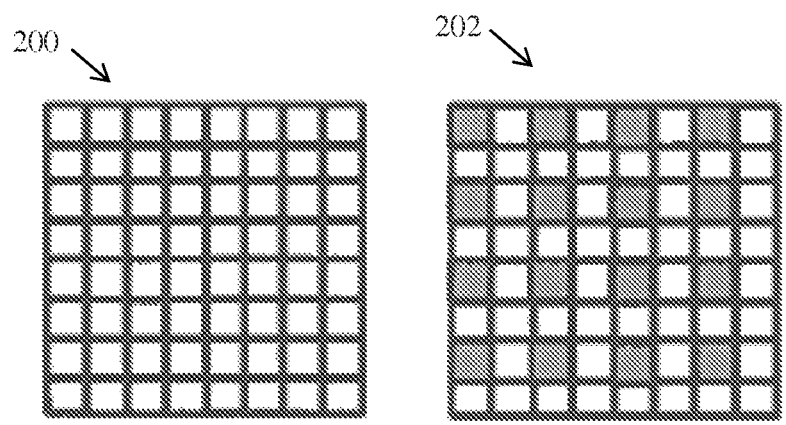
FIG. 2 illustrates an exemplary sampling pattern for sampling within an image patch according to a first embodiment of the present invention.
Figure 3:
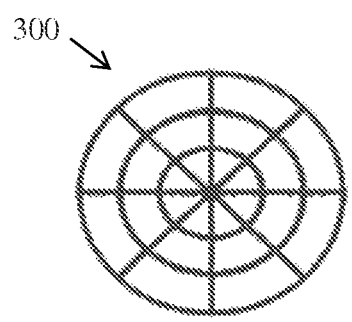
FIG. 3 illustrates an exemplary sampling pattern for sampling within an image patch according to a second embodiment of the present invention.

According to an advantageous embodiment, instead of feeding all of the voxels in a particular image patch to the trained deep neural network, a predetermined sampling pattern is used to select a subset of the set of voxels within each image to input to the trained deep neural network. FIGS. 2 and 3 illustrate two different sampling patterns that can be used to sample the subset of voxels in each image patch. It is to be understood that sampling the voxels input to the deep neural network for each image patch centered at a respective voxel in the medical image is not the same as sampling the voxels for which image patches are evaluated by the deep neural network. That is, in an advantageous embodiment, each voxel in the medical image is evaluated by the deep neural network by evaluating a respective image patch centered at each voxel in the medical image. However, each of the image patches corresponding to the voxels in the medical image is sampled to determine a subset of voxels within that image patch that are input to the deep neural network.

FIG. 2 illustrates an exemplary sampling pattern for sampling within an image patch according to a first embodiment of the present invention. In the embodiment of FIG. 2, a grid based sampling pattern 202 is used that sparsely samples an image patch 200. Although shown as squares in two dimensions in FIG. 2, the image patch 200 and the corresponding sampling pattern 202 are similarly implemented as 3D boxes when applied to 3D medical images. In this case, each small square in the image patch 200 and the corresponding sampling pattern 204 represents a voxel of the medical image. When applied to a 2D medical image, each small square represents a pixel of the 2D medical image. In one implementation, as illustrated in the example of FIG. 2, the sampling pattern 202 selects every other voxel in each dimension within the image patch. In the sampling pattern 202 of FIG. 2, the shaded squares represent the voxels that are selected by the sampling pattern 202 to be input to the deep neural network. When applied to a 20×20×20 image patch, the sampling pattern 202, which selects every other voxel in each dimension within the image patch, results in a reduction of the input vector dimension by 12.5%. Similar grid sampling pattern can also be implemented with larger step sizes as well, to achieve more aggressive sampling. In particular the grid sampling pattern can be implemented by skipping every n voxels in each direction between each voxel input to the deep neural network, where n is an integer that is greater than or equal to 1. It is also possible that a down-sampling routine be used to down-sample each image patch.

FIG. 3 illustrates an exemplary sampling pattern for sampling an image patch according to a second embodiment of the present invention. In the embodiment of FIG. 3, a log-polar sampling pattern 300 having a higher density near the patch center and a lower density when farther away from the patch center is used to select the subset of voxels to input to the deep neural network. This allows for larger distortions of object parts when far away from the center. In 2D space, the sampling pattern 300 samples pixels within a respective circular (log-polar) image patch centered at each pixel of a medical image. In 3D space, the sampling pattern 300 samples voxels a respective spherical image patch centered at each voxel of the medical image. The sampling pattern 300 divides the circular/spherical image patch into a number of regions that are smaller and closer together near the center of the image patch and larger and more spread out as the distance from the center of the image patch increases. In an advantageous implementation, a voxel closest to the centroid of each region of the sampling pattern 300 is selected to be input to the deep neural network. This results in a higher density of sampled voxels close to the center of the patch and a lower density of sampled voxels farther away from the center of the patch. In another possible implementation, the voxel values within each region of the sampling pattern 300 can be averaged, and for each region, a single voxel value representing the average of the voxels in that region can be input to the deep neural network.

Returning to FIG. 1, at step 106, the location of the landmark in the medical image is detected using the trained deep neural network based on the subset of voxels input for each of the plurality of image patches. In an advantageous application, the landmark may be an anatomical landmark that is a point (e.g., voxel) in the medical image associated with an organ or other anatomical object.

Deep neural networks are machine learning based neural networks with multiple hidden layers of learned features or variables between the input data and the output data. According to an advantageous implementation, the deep neural network will typically be implemented with three or more hidden layers. In an advantageous embodiment, the deep neural network is trained to detect a location of an anatomical landmark in medical image data. In particular, the deep neural network can be trained to detect a 2D location (x, y) of the anatomical landmark in a 2D medical image or to detect a 3D location (x, y, z) of the anatomical landmark a 3D medical image. As mentioned above, the term "voxel" is used herein to refer to an element of a medical image, regardless of the dimensionality. The deep neural network is trained based on a plurality of training images stored in a database. The training images can be 2D or 3D medical images acquired using any medical imaging modality, such as but not limited to CT, MRI, Ultrasound, X-ray fluoroscopy, DynaCT, etc. At least a subset of the training images are annotated the location of the target anatomical object. The training images may also include non-annotated images as well. In a first possible implementation, the trained deep neural can be a discriminative deep neural network that calculates, for an image patch centered at a voxel, a probability that the target landmark is located at that voxel. In a second possible implementation, the trained deep neural network can be a deep neural network regressor (regression function) that calculates, for an image patch centered at voxel, a difference vector from that voxel to a predicted location of the target landmark.

Figure 4:
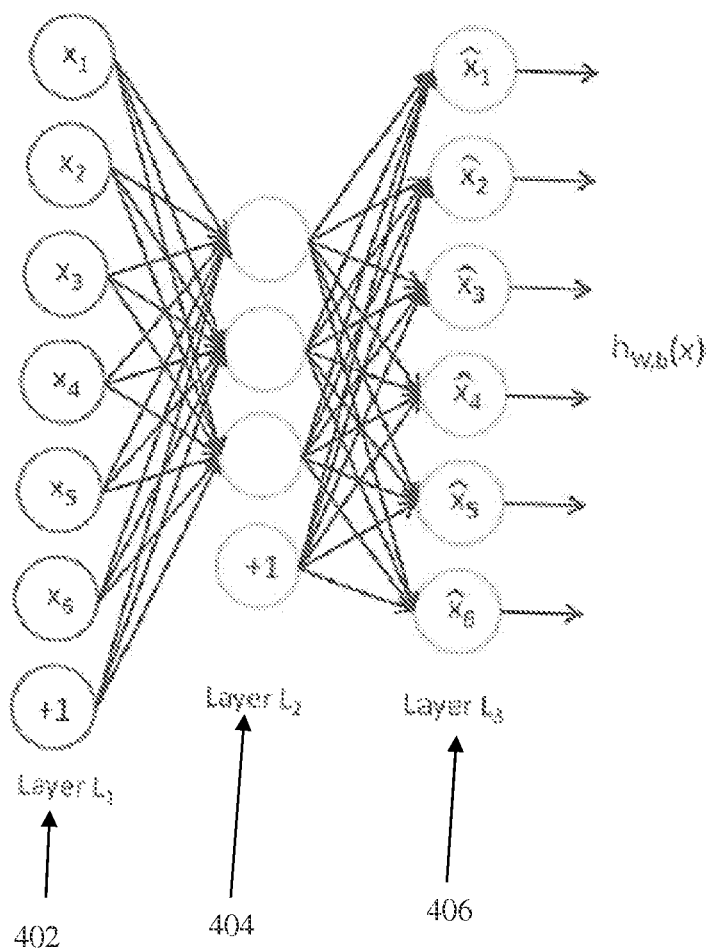
FIG. 4 illustrates an exemplary AE neural network.

The deep neural network is trained in an offline training stage prior to the landmark detection in the received medical image. The deep neural network is trained directly on the image data to learn complex image patterns and detect anatomical landmarks based on the complex image patterns. According to an advantageous embodiment of the present invention, the deep neural network is trained directly on voxels sampled from training image patches based on the predetermined sampling pattern, such as the sampling pattern of FIG. 2 or the sampling pattern of FIG. 3. A feed-forward neural network is a neural network structure with an efficient training algorithm called back-propagation. Although powerful enough to approximate complicated target functions, a large feed-forward neural network tends to over-fit the training data. It is difficult to train a network with more than two hidden layers with good generalization capability. In a possible embodiment, unsupervised pre-training followed by supervised fine-tuning can be used to overcome the over-fitting issue. This technique can be used to train networks with three or more hidden layers. The pre-training can be treated as an unsupervised learning process to discover powerful image features from the input image data. Various deep learning techniques, such as an auto-encoder (AE), denoising auto-encoder (DAE) or a restricted Boltzman machine (RBM), can be used to pre-train a hidden layer. FIG. 4 illustrates an exemplary AE neural network. As shown in FIG. 2, the AE 200 is a feed-forward neural network with one hidden layer 404. The AE 400 has an input layer $L_1$ 402, the hidden layer $L_2$, and an output layer $L_3$ 406. In an advantageous implementation, each node in the input layer 402 corresponds to a respective one of the subset of voxels (or pixels) sampled using the sampling pattern within an image patch. Ignoring the bias term (the nodes labeled as +1 in FIG. 2), the input and output layers 402 and 406, respectively have the same number of nodes. The goal of an AE is to minimize the difference between the input and output vectors. If the hidden layer 404 has a size equal to or larger than the input layer 402, an AE may learn an identify transformation. To prevent such a trivial solution, an AE can be set up with a hidden layer 404 with fewer nodes than the input layer 402. The nodes of the hidden layer 404 can be calculated as a function of a bias term and a weighted sum of the nodes of the input layer 402, where a respective weight is assigned to each connection between a node of the input layer 402 and a node in the hidden layer 404. The bias term and the weights between the input layer 402 and the hidden layer 404 are learned in the training of the AE 400, for example using a back-propagation algorithm. The nodes of the hidden layer 404 can be considered to be features extracted from the subset of voxels sampled from each image patch (represented by the nodes of the input layer 402), and the learned weights can be considered to be filters that filter the input image data to generate the features.

A denoising auto-encoder (DAE) may be used to learn a more meaningful representation of the input image data. In a DAE, a certain percentage (e.g., 50%) of the input nodes are randomly selected to be disturbed (e.g., set the value equal to zero) and the DAE is required to reconstruct the original input vector given a contaminated observation. This significantly increases the robustness of the resulting trained deep neural network. The hidden layer in a DAE may have more nodes than the input layer to achieve an over-complete representation. In an advantageous embodiment, the deep neural network is trained using a stacked denoising auto-encoder (DAE) in two stages. The first stage is unsupervised where each layer of the multi-layer deep neural network is trained to reconstruct the input image data. In this stage, after training a DAE with an output layer that reconstructs the input layer, the output layer is discarded and another DAE is stacked using the activation response of the already trained hidden layer as input to the new DAE. This process can be repeated to train and expand a network layer by layer. The second stage is supervised and the whole network error is minimized relative to the output training data starting from the pre-trained network weights. For example, in order to train a discriminative deep neural network, after pre-training a number of hidden layers, an additional layer for the target output can be added to the network and the whole network can be refined using back-propagation. Alternatively, the output of the hidden layers can be treated as high-level image features and used to train a discriminative classifier for detecting the anatomical object. In order to train a deep neural network regressor, the output parameter space can be either directly regressed using a linear function or it can be discretized relative to the parameter range (e.g., (x, y) or (x, y, z)) and solved as a multi-class classification problem. The second formulation has an advantage that it can directly encode the output probability and can generate multiple hypotheses, for example for different anatomical objects.

In step 106 of FIG. 1, the trained deep neural network evaluates each voxel in the medical image based on the subset of voxels input to the input layer of the deep neural network from the image patch centered at that voxel to detect the location of the anatomical landmark in the medical image. In the case in which the trained deep neural network is a discriminative deep neural network, the trained deep neural network calculates a probability for each voxel based on the subset of voxels input to the deep neural network from the image patch centered at that voxel, and either selects a voxel having the highest probability or clusters a number of voxels having highest probabilities to determine the location of the landmark in the medical image. In the case in which the trained deep neural network is a deep neural network regressor, the trained deep neural network calculates, for each voxel based on the subset of voxels input to the deep neural network from the image patch centered at that voxel, a displacement vector that maps the location of the voxel to a predicted location of the landmark in the medical image. The trained deep neural network can then cluster the predicted landmark locations calculated for each voxel to determine the location of the landmark in the medical image.

At step 108, the landmark detection results are output. The landmark detection results can be displayed on a display device of a computer system. For example, the medical image or a portion of the medical image can be displayed on the display device, and the landmark location can be highlighted or annotated in the displayed image. In a possible embodiment, a probability map in which each voxel of the medical image is assigned a color corresponding to a detection probability calculated for that voxel by the trained deep neural network can be displayed on the display device.

As described above, the method of FIG. 1 performs landmark detection in a medical image using a trained deep neural network. In an advantageous embodiment, the landmark detected by the trained deep neural network can be a center point of an anatomical object in the medical image, and the method of FIG. 1 can be performed to implement a first stage of detecting a pose parameters (position, orientation, and scale) for the anatomical object in the medical image in a series of marginal search spaces of increasing dimensionality in a Marginal Space Deep Learning (MSDL) or Marginal Space Deep Regression (MSDR) framework, as described in U.S. Provisional Application No. 62/148,273, filed Apr. 16, 2015, entitled "Method and System for Anatomical Object Detection Using Marginal Space Deep Neural Networks," which is incorporated herein by reference in its entirety. In this case, the trained deep neural network for the landmark detection can provide a number of position candidates, which are then used to detect position-orientation candidates in a second marginal search space, followed by detecting the full pose parameters (position, orientation, and scale) in a third marginal search space. Furthermore, in a possible implementation, image patches evaluated by the respective deep neural networks for the second and third marginal search spaces may also be sampled using one of the sampling patterns described above.

Figure 5:
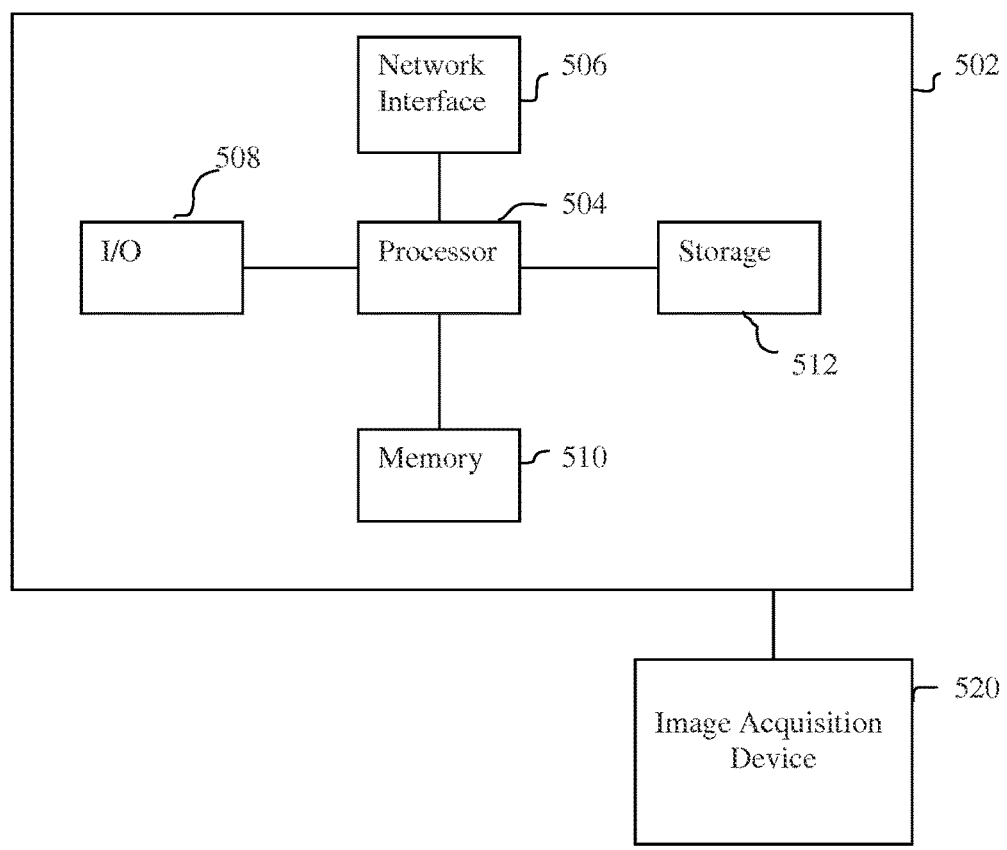
FIG. 5 is a high-level block diagram of a computer capable of implementing the present invention.

The above-described methods for landmark detection in medical image using a deep neural network may be implemented on a computer using well-known computer processors, memory units, storage devices, computer software, and other components. A high-level block diagram of such a computer is illustrated in FIG. 5. Computer 502 contains a processor 504, which controls the overall operation of the computer 502 by executing computer program instructions which define such operation. The computer program instructions may be stored in a storage device 512 (e.g., magnetic disk) and loaded into memory 510 when execution of the computer program instructions is desired. Thus, the steps of the method of FIG. 1 may be defined by the computer program instructions stored in the memory 510 and/or storage 512 and controlled by the processor 504 executing the computer program instructions. An image acquisition device 520, such as a CT scanning device, MR scanning device, Ultrasound device, etc., can be connected to the computer 502 to input image data to the computer 502. It is possible to implement the image acquisition device 520 and the computer 502 as one device. It is also possible that the image acquisition device 520 and the computer 502 communicate wirelessly through a network. In a possible embodiment, the computer 502 may be located remotely with respect to the image acquisition device 520 and the method steps can be performed as part of a server or cloud based service. The computer 502 also includes one or more network interfaces 506 for communicating with other devices via a network. The computer 502 also includes other input/output devices 508 that enable user interaction with the computer 502 (e.g., display, keyboard, mouse, speakers, buttons, etc.). Such input/output devices 508 may be used in conjunction with a set of computer programs as an annotation tool to annotate volumes received from the image acquisition device 520. One skilled in the art will recognize that an implementation of an actual computer could contain other components as well, and that FIG. 5 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for landmark detection in a medical image comprising:
   for each of a plurality of image patches centered at a respective one of a plurality of voxels in the medical image, inputting a subset of voxels within the image patch to a trained deep neural network based on a predetermined sampling pattern, wherein the predetermined sampling pattern selects a higher density of voxels to be input to the trained deep neural network near a center of the image patch and a lower density of voxels to be input to the trained deep neural network farther away from the center of the image patch; and
   detecting a location of a target landmark in the medical image using the trained deep neural network based on the subset of voxels input to the trained deep neural network from each of the plurality of image patches.

2. The method of claim 1, wherein the predetermined sampling pattern is a log-polar sampling pattern.

3. The method of claim 2, wherein the log-polar sampling pattern divides the image patch into a plurality of regions, wherein regions closer to the center of the image patch are smaller than regions farther away from the image patch, and for each of the plurality of regions of the image patch, selects a voxel closest to a centroid of that region to be input to the trained deep neural network.

4. The method of claim 2, wherein the log-polar sampling pattern divides the image patch into a plurality of regions, wherein regions closer to the center of the image patch are smaller than regions farther away from the image patch, and for each of the plurality of regions of the image patch, calculates an average of voxel values in that region and inputs a voxel having an average voxel value for that region to the trained deep neural network.

5. The method of claim 1, wherein the trained deep neural network is a discriminative deep neural network and detecting a location of a target landmark in the medical image using the trained deep neural network based on the subset of voxels input to the trained deep neural network from each of the plurality of image patches comprises:
   calculating a probability for each of the plurality of voxels in the medical image based on the subset set of voxels input to the trained deep neural network within the respective image patch centered at each of the plurality of voxels; and
   detecting the location of the target landmark as a location of one of the plurality of voxels in the medical image with a highest probability.

6. The method of claim 1, wherein the trained deep neural network is a deep neural network regressor and detecting a location of a target landmark in the medical image using the trained deep neural network based on the subset of voxels input to the trained deep neural network from each of the plurality of image patches comprises:
   for each of the plurality of voxels in the medical image, calculating a displacement vector that maps that voxel to a predicted location of the target landmark in the medical image, based on the subset set of voxels input to the trained deep neural network within the respective image patch centered at that voxel; and detecting the location of the target landmark by clustering the predicted locations of the target landmark calculated for each of the plurality of voxels in the medical image.

7. The method of claim 1, wherein the trained deep neural network is trained based on a respective subset of voxels sampled within each of a plurality of training image patches using the predetermined sampling pattern.

8. An apparatus for landmark detection in a medical image comprising:

means for inputting, for each of a plurality of image patches centered at a respective one of a plurality of voxels in the medical image, a subset of voxels within the image patch to a trained deep neural network based on a predetermined sampling pattern, wherein the predetermined sampling pattern selects a higher density of voxels to be input to the trained deep neural network near a center of the image patch and a lower density of voxels to be input to the trained deep neural network farther away from the center of the image patch; and means for detecting a location of a target landmark in the medical image using the trained deep neural network based on the subset of voxels input to the trained deep neural network from each of the plurality of image patches.

9. The apparatus of claim 8, wherein the predetermined sampling pattern is a log-polar sampling pattern.

10. The apparatus of claim 9, wherein the log-polar sampling pattern divides the image patch into a plurality of regions, wherein regions closer to the center of the image patch are smaller than regions farther away from the image patch, and for each of the plurality of regions of the image patch, selects a voxel closest to a centroid of that region to be input to the trained deep neural network.

11. The apparatus of claim 9, wherein the log-polar sampling pattern divides the image patch into a plurality of regions, wherein regions closer to the center of the image patch are smaller than regions farther away from the image patch, and for each of the plurality of regions of the image patch, calculates an average of voxel values in that region and inputs a voxel having an average voxel value for that region to the trained deep neural network.

12. The apparatus of claim 8, wherein the trained deep neural network is trained based on a respective subset of voxels sampled within each of a plurality of training image patches using the predetermined sampling pattern.

13. A non-transitory computer readable medium storing computer program instructions for landmark detection in a medical image, the computer program instructions when executed by a processor cause the processor to perform operations comprising:

for each of a plurality of image patches centered at a respective one of a plurality of voxels in the medical image, inputting a subset of voxels within the image patch to a trained deep neural network based on a predetermined sampling pattern, wherein the predetermined sampling pattern selects a higher density of voxels to be input to the trained deep neural network near a center of the image patch and a lower density of voxels to be input to the trained deep neural network farther away from the center of the image patch; and detecting a location of a target landmark in the medical image using the trained deep neural network based on the subset of voxels input to the trained deep neural network from each of the plurality of image patches.

14. The non-transitory computer readable medium of claim 13, wherein the predetermined sampling pattern is a log-polar sampling pattern.

15. The non-transitory computer readable medium of claim 14, wherein the log-polar sampling pattern divides the image patch into a plurality of regions, wherein regions closer to the center of the image patch are smaller than regions farther away from the image patch, and for each of the plurality of regions of the image patch, selects a voxel closest to a centroid of that region to be input to the trained deep neural network.

16. The non-transitory computer readable medium of claim 14, wherein the log-polar sampling pattern divides the image patch into a plurality of regions, wherein regions closer to the center of the image patch are smaller than regions farther away from the image patch, and for each of the plurality of regions of the image patch, calculates an average of voxel values in that region and inputs a voxel having an average voxel value for that region to the trained deep neural network.

17. The non-transitory computer readable medium of claim 13, wherein the trained deep neural network is a discriminative deep neural network and detecting a location of a target landmark in the medical image using the trained deep neural network based on the subset of voxels input to the trained deep neural network from each of the plurality of image patches comprises:

calculating a probability for each of the plurality of voxels in the medical image based on the subset set of voxels input to the trained deep neural network within the respective image patch centered at each of the plurality of voxels; and detecting the location of the target landmark as a location of one of the plurality of voxels in the medical image with a highest probability.

18. The non-transitory computer readable medium of claim 13, wherein the trained deep neural network is a deep neural network regressor and detecting a location of a target landmark in the medical image using the trained deep neural network based on the subset of voxels input to the trained deep neural network from each of the plurality of image patches comprises:

for each of the plurality of voxels in the medical image, calculating a displacement vector that maps that voxel to a predicted location of the target landmark in the medical image, based on the subset set of voxels input to the trained deep neural network within the respective image patch centered at that voxel; and detecting the location of the target landmark by clustering the predicted locations of the target landmark calculated for each of the plurality of voxels in the medical image.

19. The non-transitory computer readable medium of claim 13, wherein the trained deep neural network is trained based on a respective subset of voxels sampled within each of a plurality of training image patches using the predetermined sampling pattern.

* * * * *